United States Patent [19]
Grier-Idris

[11] Patent Number: 5,197,493
[45] Date of Patent: Mar. 30, 1993

[54] INCISE SYSTEM

[75] Inventor: Carletta Grier-Idris, Acworth, Ga.

[73] Assignee: Kimberly-Clark Corporation, Neenah, Wis.

[21] Appl. No.: 852,915

[22] Filed: Mar. 13, 1992

Related U.S. Application Data

[63] Continuation of Ser. No. 450,878, Dec. 14, 1989, abandoned.

[51] Int. Cl.$^5$ .............................................. A61B 19/08
[52] U.S. Cl. ..................... 128/853; 128/849; 128/850; 602/58
[58] Field of Search ................... 602/58; 128/849, 850, 128/851, 852, 853, 888

[56] References Cited

U.S. PATENT DOCUMENTS

| | | | |
|---|---|---|---|
| Re. 31,886 | 5/1885 | Hodgson | 428/40 |
| Re. 31,887 | 5/1985 | Hodgson | 428/355 |
| 3,799,161 | 3/1974 | Collins | 128/132 D |
| 3,826,253 | 7/1974 | Yarsh et al. | 128/132 D |
| 3,856,006 | 12/1974 | Krzewinski | 128/132 D |
| 3,916,887 | 11/1975 | Kelly | 128/132 D |
| 4,024,862 | 5/1977 | Collins | 128/132 D |
| 4,169,472 | 10/1979 | Morris | 128/132 D |
| 4,310,509 | 1/1982 | Berglund et al. | 428/28 |
| 4,316,455 | 2/1982 | Stoneback | 128/853 |
| 4,323,557 | 4/1982 | Rosso et al. | 428/28 |
| 4,336,797 | 6/1982 | Latucca et al. | 128/132 D |
| 4,452,845 | 6/1984 | Lloyd et al. | 428/220 |
| 4,489,720 | 11/1984 | Morris et al. | 128/132 D |
| 4,524,767 | 6/1985 | Glassman | 128/132 D |
| 4,616,641 | 10/1986 | Teeple | 128/132 R |
| 4,641,643 | 2/1987 | Greer | 128/156 |
| 4,681,574 | 7/1987 | Eastman | 604/344 |
| 4,730,609 | 3/1988 | McConnell | 128/132 D |

FOREIGN PATENT DOCUMENTS 0166124 1/1986 European Pat. Off. .
2120104 5/1982 United Kingdom .

OTHER PUBLICATIONS

Smith and Nephew Brochure–entitled–"Opsite Incise the Original Membrane Surgical Drape".
"Peel Adhesion for Single Coated Tapes 180° Angle'-'–Call Letters PSTC-1–Nov. 1970.
"Adhesion to Fiberboard at 90 Degree Angle and Constant Stress"–Call Letters-PSTC-14–Nov. 1970.

*Primary Examiner*—Paul Prebilic
*Attorney, Agent, or Firm*—Patrick C. Wilson

[57] ABSTRACT

Disclosed herein is an incise system for surgical drapes and the resultant surgical drape. The incise system is a two layer structure including a first layer of incise with an adhesive bottom surface for adhering the layer to a surgical drape and/or the skin of a patient. The first layer of incise further defines a fenestrated area removably attached to the remainder of the first layer by a line of perforations. The second layer of incise is generally coextensive with and releasably attachable to the first layer of incise so as to cover the fenestrated area of the river layer.

To use the incise system of the present invention the two layer structure is applied to the patient's skin such that the fenestrated area of the first layer of incise directly overlies the intended incision area. An incision can then be made directly through the two layers of incise. Once the procedure is completed, the top (second) layer of incise is peeled from the bottom (first) layer. In so doing, the top layer also removes the perforated fenestration area from the first layer thereby exposing a portion of the patient's skin surrounding the incision. As a result, suturing of the incision is made easier since it is no longer necessary to pick and peel the incise away from the incision to expose sufficient skin to allow suturing without catching the incise in the process.

9 Claims, 3 Drawing Sheets

INCISE SYSTEM

This is a continuation of copending application Ser. No. 07/450,878 filed on Dec. 14, 1989 now abandoned.

BACKGROUND OF THE INVENTION

The present invention relates to an incise material suitable for use in surgical procedures. More specifically, the incise material is a two layer structure which has a removable top layer to facilitate suturing of an incision upon completion of a surgical procedure.

Many of today's surgical procedures involve the use of an incise material. An incise material is usually a clear polymeric film with an adhesive on one side which is in turn covered with a release paper. Two suppliers of incise material are the Minnesota Mining and Manufacturing Company and T. J. Smith and Nephew Ltd. Examples of incise material can be found, by way of example only, in U.S. Pat. Nos. 4,310,509; 4,323,557; 4,452,845; Re. 31,886 and Re. 31,887. Most typically incise material is used in connection with towels or surgical drapes to maintain the surgical area as clean and sterile as possible to help reduce the risk of postoperative infection. Once the surgical area of the patient has been scrubbed and treated with a bacteriostat, the surgical site is squared-off by the use of sterile towels or a surgical drape which has a fenestration of a size which is larger than the expected size of the incision. An incise material is then used to cover all or a portion of the patient's skin left exposed by the towels or the fenestration in the surgical drape or mainsheet. Some surgeons prefer to use incise materials which themselves have fenestrations which are only slightly larger than the incision area. Other surgeons prefer to use incise materials which completely cover the incision area with the incision being made directly through the incise material. In either case, to apply the incise the releasable backing is removed and the adhesive side of the material is applied directly to the skin of the patient. One purpose in using the incise material is to help reduce the migration of germs and bacteria to the incision site. This is because, despite the cleansing of the skin, the pores still contain additional germs and bacteria which can migrate to the surface as the skin is moved and worked during the course of the surgical procedure. By covering the skin, it has been found that this migration can be reduced.

When an incise is used which completely covers the incision area the surgeon will cut right through the incise material attached to the skin. In this manner the amount of exposed skin surrounding the incision is minimized. A problem arises, however, when it comes time to close the incision. At this point the incise material directly surrounding the incision must be peeled back so as to expose sufficient skin for the suturing procedure. This process of peeling the incise back is, at the very least, a time consuming and annoying process. Because of this problem, some surgeons elect to use the above-described fenestrated incise material to eliminate the need for peeling back the incise material. This, however, is often a compromise decision since, in using a fenestrated incise material, more skin is exposed about the incision site thereby increasing the risk of bacteria and germs making their way to the incision and causing infection.

It is therefore an object of the present invention to provide an incise system which will allow the surgeon to cut directly through the incise material while at the same time permitting easy exposure of the skin about the incision when it comes time to close the incision. This and other objects of the present invention will become more apparent upon a further review of the following specification, drawings and claims.

SUMMARY OF THE INVENTION

As described in more detail below, disclosed herein is an incise system for surgical drapes and the resultant surgical drape. The incise system is a two layer structure including a first layer of incise with an adhesion bottom surface for adhering the layer to a surgical drape and/or the skin of a patient. The first layer of incise further defines a fenestrated area removably attached to the remainder of the first layer by a line of perforations. The second layer of incise is generally coextensive with and releasably attachable to the first layer of incise so as to cover the fenestrated area of the first layer.

To use the incise system of the present invention the two layer structure is applied to the patient's skin such that the fenestrated area of the first layer of incise directly overlies the intended incision area. An incision can then be made directly through the two layers of incise. Once the procedure is completed, the top (second) layer of incise is peeled from the bottom (first) layer. In so doing, the to player also removes the perforated fenestration area from the first layer thereby exposing a portion of the patient's skin surrounding the incision. As a result, suturing of the incision is made easier since it is no longer necessary to pick and peel the incise away from the incision to expose sufficient skin to allow suturing without catching the incise in the process.

DESCRIPTION OF THE PREFERRED EMBODIMENT

Figure 1:
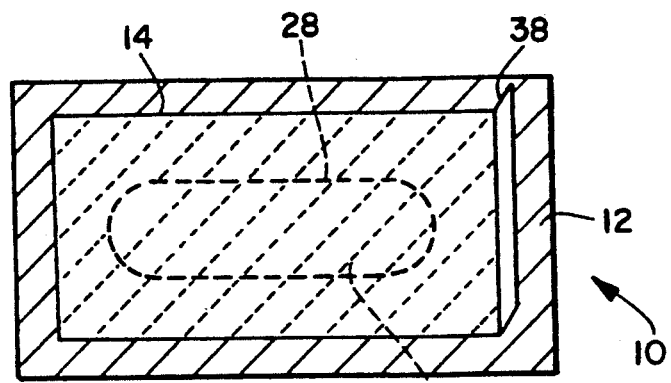
FIG. 1 is a top plan view of an incise system according to the present invention.

Referring to FIGS. 1 through 7 there is shown an incise system 10 according to the present invention. The incise system 10 is comprised of a first layer 12 and a second layer 14 of incise. Such incise is readily available and well known to those having ordinary skill in the art. Examples of an incise including adhesive suitable for the present invention include Opsite ® Incise 63110; 63210; 63310 and 63410 from T. J. Smith and Nephew Inc., 2000 South Beltline Blvd., Columbia, S.C., U.S.A. 29205. The incise system 10 including the first layer 12 and second layer 14 may be manufactured and sold as a separate unit or it may be sold as part of a surgical pack in which case the system 10 may be unattached or pre-attached to a surgical drape or mainsheet 11 having a primary fenestration 13, a top edge 8 and a bottom edge 9 joined by a pair of opposed side edges 15 and 17. The mainsheet 11 further includes a top surface 19 and a bottom surface 21. See FIG. 3. In any event, the first layer 12 should be of a size sufficient to cover all sides of the fenestration 13 in the surgical drape 11.

Figure 2A:
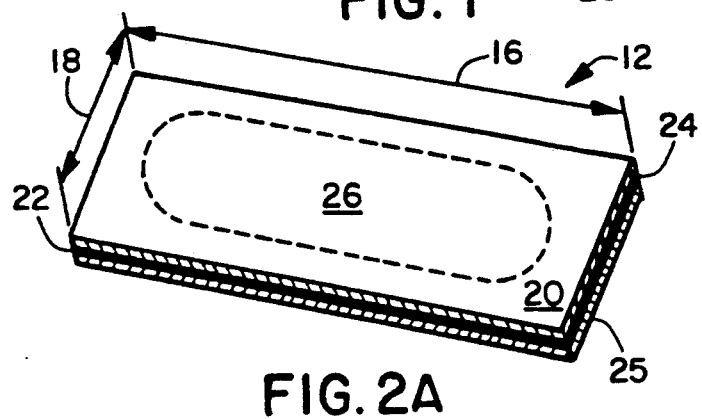
FIG. 2A is a perspective view of the first or bottom layer of an incise system according to the present invention.
Figure 2B:
FIG. 2B is a side view of the material shown in FIG. 2A.

Referring to FIGS. 2A and 2B, the first layer 12 is a continuous layer of incise having a first length 16 and a first width 18. The first layer 12 has a top surface 20 and a bottom surface 22. Affixed to the bottom surface 22 is a first adhesive layer 24, the composition of which is well known to those having ordinary skill in the art. Attached to the first adhesive layer 24 is a release paper 25, the composition of which is also well known to those having ordinary skill in the art. Additionally, the first layer 12 has a separate removable fenestrated area 26 located within and connected to the first layer 12 by a line of perforations 28 which will permit the fenestrated area 26 to be separated from the remainder of the first layer 12 when sufficient force is exerted on the perforations 28. The fenestration area 26 should generally be at least an inch longer at either end than the intended length of the incision. The width of the fenestration area 26 should also generally be at least an inch wider on either side of the incision. This will assure that their is sufficient skin exposed to permit suturing.

Figure 2C:
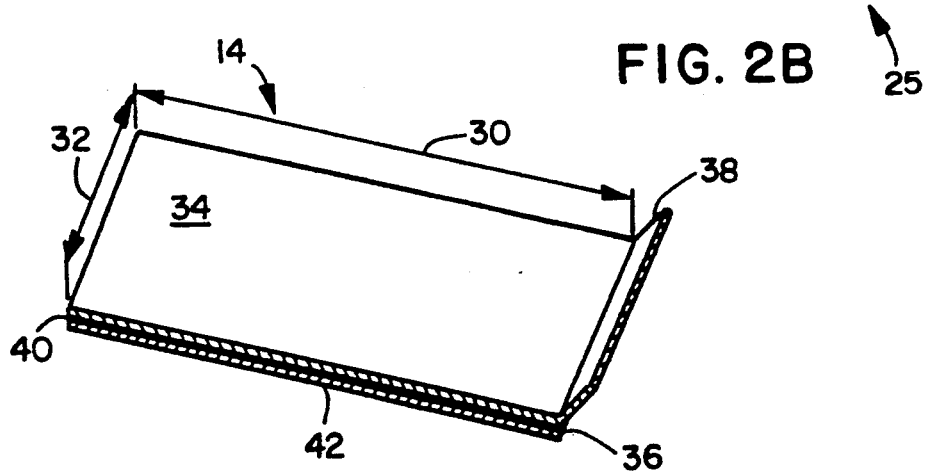
FIG. 2C is a perspective view of the second or top layer of an incise system according to the present invention.
Figure 2D:
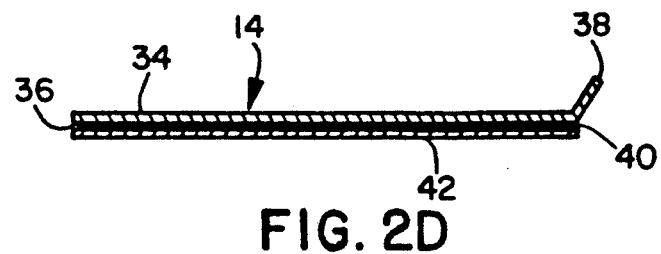
FIG. 2D is a side view of the material shown in FIG. 2C.
Figure 7:
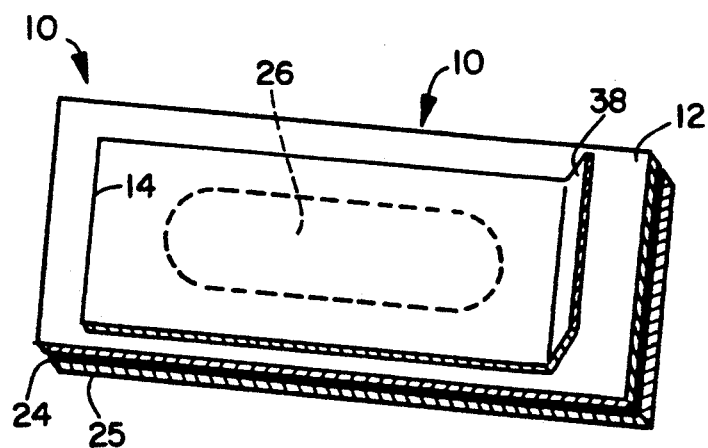
FIG. 7 is another perspective view of an incise system according to the present invention.

Referring to FIGS. 2C and 2D, the second layer of incise 14 is a continuous sheet having a second length 30 and a second width 32 which are generally coextensive with the first length 16 and first width 18 of the first layer 12. Layer 14 also has a top surface 34 and a bottom surface 36. As shown in FIGS. 1 and 7, first layer 12 is slightly larger than the second layer 14, however, the first layer 12 also may be smaller than or equal in size to the second layer 14 so long as the second layer 14 covers the perforated fenestration area 26 of the first layer 12. To facilitate removal of the second layer 14 from the first layer 12, the second layer 14 may be provided with one or more pull tabs 38 located along the edges of the second layer 14. In its simplest form the pull tab 38 may be a section of the second layer 14 folded over and adhered to itself via an adhesive. Alternatively, the pull tab 38 may be a separate element such as an adhesive-coated paper with instructions or other indicia located thereon and affixed to one of the ends of the second layer 14. The tab 38 should be of sufficient size to permit adequate grasping and pulling of the tab 38 when releasing the second layer 14 from the first layer 12. Generally a height of one inch or more should suffice.

Figure 5:
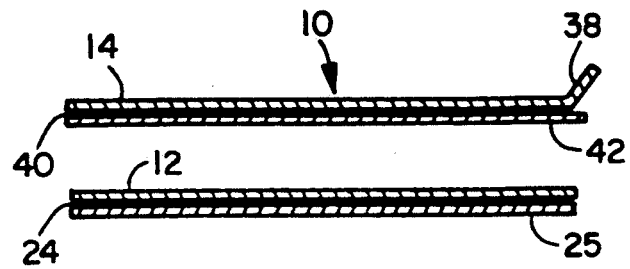
FIG. 5 is a side view of the first and second layers of incise with separate release liners according to the present invention.
Figure 6:
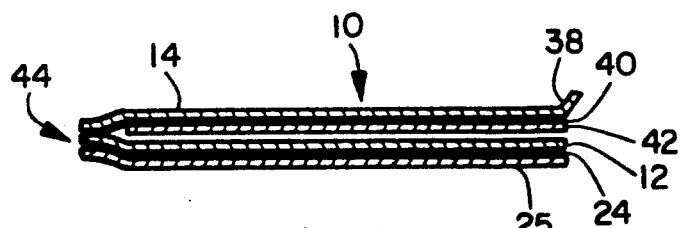
FIG. 6 is a side view of a first and second layer of incise when joined along a common edge according to the present invention.

To releasably adhere the first layer 12 and the second layer 14 together, a second adhesive layer 40 similar to the previously mentioned adhesive layer 24 is positioned between the two layers 12 and 14. This second adhesive layer 40 may be applied to the top surface 20 of the first layer 12 or to the bottom surface 36 of the second layer 14. In FIG. 2D the adhesive layer 40 is shown attached to the bottom surface 36 of the second layer 14. Generally, the two layers 12 and 14 are adhered to one another during the manufacturing of the present invention so that the two layers may be applied together to the patient's skin thereby lessening the chance of wrinkling. See FIG. 2E. Alternatively, however, as shown in FIG. 2D a release liner 42 may be attached to one side of the exposed second adhesive layer 40 to keep the two layers 12 and 14 separated until attachment of the two layers is desired. In such a configuration, the first and second layers 12 and 14 may be completely separated as shown in FIG. 5. On the other hand, the two layers 12 and 14 may be joined along a common edge 44 as shown in FIG. 6. In addition, this common edge 44 may be attached to the top surface 19 of the mainsheet 11 adjacent the fenestration 13. Most commonly this edge 44 is opposite the pull tab 38. Furthermore, the release paper 42 should not extend completely across the juxtaposed bottom surface 36 of second layer 14 and the top surface 20 of the bottom layer 12. Instead, the release paper 42 should extend from the end of the layers 12 and 14 adjacent the pull tab 38 to a point adjacent the joined common edge 44. In this manner the adhesive 40 can be used to adhere and hinge the two layers 12 and 14 together. See FIG. 6.

Figure 3:
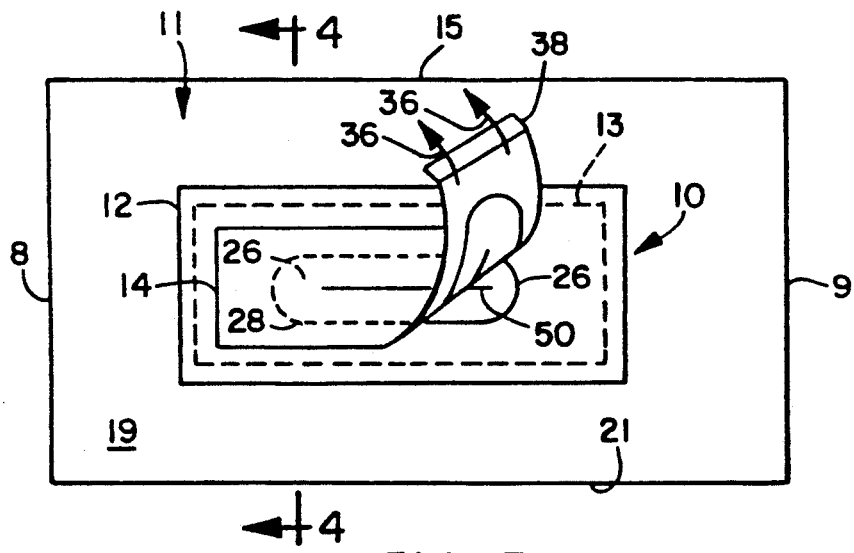
FIG. 3 is a top plan view of an incise system according to the present invention attached to a surgical drape with the second layer of incise being separated from the first layer.
Figure 4:
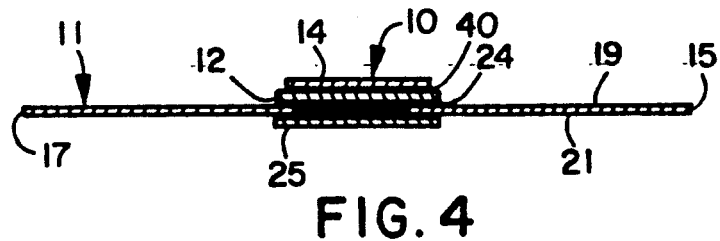
FIG. 4 is a cross-sectional view of FIG. 3 taken along line 4—4.

As stated at the outset, the incise system 10 of the present invention may be either unattached to the drape (as shown in FIGS. 1, 5, 6 and 7) or preattached (as shown in FIGS. 3 and 4). When the incise system is attached to the drape 11, it should be large enough to cover the fenestration 13 in the drape 11 as shown in FIGS. 3 and 4. Also, in most cases the release paper 25 will be attached to the underside of the drape 11 as shown in cross-section in FIG. 4 via the adhesive layer 24.

Having thus described several embodiments of the noise system 10, the application and removal of the system will be explained.

When the incise system 10 of the present invention is preattached to a surgical drape as is the case in FIGS. 3 and 4, the drape 11 is applied to the patient in the same manner as would normally be prescribed for the specific type of drape. To apply the incise, the release paper 25 is removed thereby exposing the adhesive 24 for adhesion to the patient's skin (not shown) in the intended area of the surgical procedure. The only added precaution is that the fenestrated area 26 be properly aligned so that the incision 50 is made within the confines of the fenestrated area 26. Once the drape 11 and incise system 10 are in place, an incision 50 can be made through layer 12, the fenestrated area 26 of layer 14 and the patient's skin within the area defined by fenestrated area 26. Both the skin and incise can then be pulled back and clamped to facilitate the surgical procedure.

To use the incise system shown in FIG. 5 which employs two release papers 25 and 42, the two layers are applied in sequence with the first layer 12 being first applied to the skin of the patient (not shown) followed by the application of layer 14. As with the first embodiment, once the system has been applied, an incision is made in the skin through the two layers of incise 12 and 14 in the area of the perforated fenestration area 26 of layer 12. Both the skin and the incise can then be pulled back and clamped to facilitate the surgical procedure.

Figure 2E:
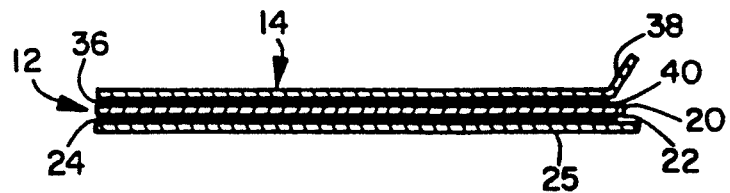
FIG. 2E is a side view of an incise system according to the present invention.

To use the incise system 10 shown in FIGS. 2E and 7, the release paper 25 is removed from the bottom 22 of the system 10 thereby exposing the adhesive 24 on the bottom of the first layer 12. The adhesive side is then applied to the skin (not shown) of the patient and an incision is made through the skin and the area of the second layer 14 which directly overlies the fenestration area 26 in the first layer 12. Both the skin and the incise can then be pulled back and clamped to facilitate the surgical procedure.

To use the incise system 10 shown in FIG. 6, the release paper 25 is removed from the bottom 22 of the system 10 thereby exposing the adhesive 24 on the bottom of the first layer 12. The adhesive 24 is applied to the patient's skin such that the fenestrated area 26 directly overlies the intended site of the incision. Next, the release liner 42 is removed from the second layer of incise 14 thereby exposing the adhesive 40 for adhesion of the second layer 14 to the top of the first layer 12. As with the other embodiments, once the system 10 has been applied, an incision is made through the skin (not shown) and the two layers of incise 12 and 14 in the area of the perforated fenestration area 26 of layer 12. Both the skin and the incise can then be pulled back and clamped to facilitate the surgical procedure.

Once the procedure has progressed to the point of closure, the top or second layer 14 is removed by grasping and pulling the tab 38 in the direction of arrows 36 as shown in FIG. 3. As the second layer is pulled/peeled back, the perforated fenestration area 26 of first layer 12 is removed along with the second layer 14 thereby providing an area of exposed skin about the incision to permit suturing without interference from the incise material. To ensure the fenestrated area 26 of the first layer 12 is peeled off along with the second layer 14, the adhesive peel strength of the second layer 14 should be great enough to overcome the force of the adhesive 24 holding the fenestrated area 26 to the patient's skin and the force needed to separate the perforated fenestration area 26 from the remainder of the first layer 12. Consequently, the peel strength of the second layer 14 (second peel strength) should be greater than that of the first layer 12 (first peel strength). One standard that can be used to measure such peel forces/strengths is PSTC-1 (November 1970 revised version of the September 1955 test) developed by the Pressure Sensitive Tape Council, 1201 Waukegan Road, Glenview, Ill.60025. Also note that to make separation of the perforated fenestration area 26 from the remainder of first layer 12 easier, the number of perforations 28 can be increased. Note too that in removing the second layer 14 from the first layer 12 it may be necessary to hold down the first layer 12 to assist in keeping the lower layer 12 from separating prematurely from the skin of the patient. Finally, having completed the suturing, the first layer 12 of incise may be removed from the patient, most commonly in conjunction with the removal of the main sheet 11.

Having thus described the invention in detail it should be appreciated that various other modifications can be made without departing from the spirit and scope of the appended claims. For example, the fenestrated area 26 instead of being located entirely within the incise may extend over to one edge of the incise to create a "U-shaped" or other cut-out portion for limb surgery.

I claim:
1. An incise system for use in surgical procedures comprising:
   a first layer of incise material having a first length and a second width, a top surface and a bottom surface, said first layer of incise defining a fenestration area removably attached to the remainder of said first layer of incise by a line of perforations, and
   a second layer of incise releasably attachably to said top surface of said first layer of incise, said second layer of incise having a second length and a second width sufficient to cover said fenestration area in said first layer of incise, said second layer of incise having an adhesion to said top surface of said first layer of incise sufficient to detach said fenestrated area from said first layer of incise when said second layer is released from said first layer of incise,
   said first layer of incise having a first peel strength and said second layer of incise having a second peel strength, said second peel strength being greater than said first peel strength so that said fenestrated area is separated from said first layer of incise.
2. The incise system of claim 1 which further includes a release liner releasably attached to said bottom surface of said first layer of incise.
3. The incise system of claim 2 wherein said second layer of incise further includes a top surface and a bottom surface with a release liner releasably attached to said bottom surface of said second layer of incise.
4. The incise system of claim 1 wherein said second layer of incise has a pull tab attached thereto to facilitate removal of said second layer of incise and said fenestrated area of said first layer of incise from said first layer of incise.
5. The incise system of claim 1 wherein siad first and second layers of incise are attached to one another along a common edge.
6. A surgical drape comprising:
   a mainsheet having a top edge and a bottom edge joining be a pair of opposed side edges and further having a top surface and a bottom surface, said mainsheet also defining a primary fenestration therein, and
   a two layer incise system for covering said primary fenestration including a first layer and a second layer of incise joined along a common edge,
   said first layer of incise having a first length and a first width, a top surface, and a bottom surface for adhering said first layer of incise to said mainsheet to cover said primary fenestration of said mainsheet, said first layer of incise defining a fenestrated area removably attached to the remainder of said first layer of incise by a line of perforations,
   said second layer of incise being releasably attachable to said top surface of said first layer of incise, said second layer of incise having a second length and a second width sufficient to cover said fenestrated area in said first layer of incise, said second layer of incise having a pull tab attached thereto along an edge opposite to said common edge to facilitate separation of said second layer of incise and said fenestrated area of said first layer of incise from said first layer of incise;
   said first layer of incise having a first peel strength and said second layer of incise having a second peel strength, said second peel strength being greater than said first peel strength so that siad fenestrated area is separated from said first layer of incise.

7. The surgical drape of claim 6 wherein said first layer of incise and said second layer of incise each have a release liner removably attached thereto.

8. The surgical drape of claim 6 which further includes a release liner located adjacent said bottom surface of said mainsheet and releasably attached to said bottom surface of said first layer of incise in the area of said primary fenestration of said mainsheet.

9. The surgical drape of claim 6 wherein said first and second layers of incise are attached to one another along a common edge with said common edge being attached to said top surface of said mainsheet adjacent said primary fenestration.

* * * * *

UNITED STATES PATENT AND TRADEMARK OFFICE
CERTIFICATE OF CORRECTION

PATENT NO. : 5,197,493

DATED : March 30, 1993

INVENTOR(S) : Carletta Grier-Idres

It is certified that error appears in the above-identified patent and that said Letters Patent is hereby corrected as shown below:

On the title page:
Abstract, line 11, "river layer" should read --first layer--;

Column 2, line 12, "adhesion bottom" should read --adhesive bottom--;

Column 2, line 29, "to player" should read --top layer--;

Column 4, line 42, "the noise" should read --the incise--;

Column 6, line 9, "attachably to" should read --attachable to--;

Column 6, line 40, "joining be" should read --joined by--;

Column 6, line 67, "that siad" should read --that said--;

Column 6, line 5, "second width" should read --first width--;

Signed and Sealed this

Fourteenth Day of November, 1995

Attest:

BRUCE LEHMAN

Attesting Officer

Commissioner of Patents and Trademarks